United States Patent [19]
Bitowft et al.

[11] Patent Number: 5,922,165
[45] Date of Patent: *Jul. 13, 1999

[54] PROCESS TO PRODUCE SANITARY NAPKINS WITH LOW TOLERANCE BETWEEN CRIMPED SIDE SEAL AND ABSORBENT CORE

[75] Inventors: Bruce Kevin Bitowft, Glashutten; Karsten Puchert, Griesheim, both of Germany

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,495

[22] PCT Filed: Jun. 7, 1995

[86] PCT No.: PCT/US95/07252

§ 371 Date: Dec. 20, 1996

§ 102(e) Date: Dec. 20, 1996

[87] PCT Pub. No.: WO96/00547

PCT Pub. Date: Jan. 11, 1996

[30] Foreign Application Priority Data

Jun. 28, 1994 [EP] European Pat. Off. .............. 94109926

[51] Int. Cl.⁶ .................................................... A61F 13/15
[52] U.S. Cl. ...................... 156/308.4; 156/196; 156/292; 264/324
[58] Field of Search .................................... 156/164, 196, 156/292, 209, 308.4; 604/387, 383, 389, 390, 354, 373; 428/74; 264/324

[56] References Cited

U.S. PATENT DOCUMENTS

| | | |
|---|---|---|
| 3,666,611 | 5/1972 | Joa . |
| 4,079,739 | 3/1978 | Whitehead ........................ 604/387 X |
| 4,184,902 | 1/1980 | Karami . |
| 4,493,868 | 1/1985 | Meitner .............................. 156/290 X |
| 4,592,708 | 6/1986 | Feist et al. . |
| 4,678,527 | 7/1987 | Ulman ................................ 156/164 X |
| 4,859,388 | 8/1989 | Peterson et al. . |
| 5,057,357 | 10/1991 | Winebarger ........................ 156/290 X |
| 5,064,492 | 11/1991 | Friesch . |

FOREIGN PATENT DOCUMENTS

| | | |
|---|---|---|
| 0 176 853 A1 | 4/1986 | European Pat. Off. . |
| 0429393 | 5/1991 | European Pat. Off. . |
| 8 902 635 | 5/1991 | Netherlands . |
| WO 90/13278 | 11/1990 | WIPO . |
| 9116870 | 11/1991 | WIPO .................................. 604/383 |

OTHER PUBLICATIONS

English abstract of E. P. 429,393.

*Primary Examiner*—Jeff H. Aftergut
*Attorney, Agent, or Firm*—Theodore P. Cummings; Jeffrey V. Bamber; Jacobus C. Rasser

[57] ABSTRACT

A process to make a profiled disposable absorbent product is disclosed. The disposable absorbent product has a first sheet, a second sheet and a fibrous core. The core is disposed between the first and second sheets and both sheets are joined to each other along a continuous or discontinuous line. The process comprises the steps of joining the first sheet to the second sheet along a line following at least part of the periphery of the core with a distance to the core of 3 mm to 8 mm; and calendering the core between the sheets in a calender to approximately uniform density, the calendering being such that the core expands along its periphery and thereby reduces the distance of between the edge of the core and the line joining the first sheet to the second sheet by 1 mm or more. The process provides absorbent articles with very small distances between the core and the line of joining the topsheet and backsheet of the absorbent article.

10 Claims, No Drawings

PROCESS TO PRODUCE SANITARY NAPKINS WITH LOW TOLERANCE BETWEEN CRIMPED SIDE SEAL AND ABSORBENT CORE

FIELD OF THE INVENTION

The invention relates to a process for making a sanitary napkin having an absorbent core between a topsheet and a backsheet and a crimped side seal combining the topsheet and the backsheet around the core. In particular the process relates to making a product which has a small distance between the core and the crimped side seal of a sanitary napkin.

BACKGROUND OF THE INVENTION

Historically the distance between the core edge and the side seal had to be fairly large, typically up to 10 mm, in order to accommodate variation, e.g,. caused by core growth during calendering of the core prior to crimping. The process now devised uses a series of calandering steps to reduce this variation and hence allow the core edge and side seal to be much closer. With a calandering step after forming the side seal it becomes possible to make sanitary napkins having a small or even no distance between the core edge and the crimped side seal.

Absorbent products are typically made out of three layers: a liquid impervious backsheet; a liquid pervious topsheet; and an absorbent core sandwiched between the backsheet and the topsheet. When putting these three parts together during the manufacturing of absorbent products it is usual to have endless backsheet roll material and topsheet roll material guided from above and below around a discontinuous absorbent core structure.

The topsheet and backsheet are joined to each other at a certain distance to the core in order to accommodate the variation of core dimensions due to the variation introduced when making the core. The joining can be continues or discontinues. The distance also has to accommodate the alignment variations between core and the joining, equipment. The resulting product therefore necessarily has a certain distance between the edge of the core and the innermost line of the edge of the joining between the topsheet and the backsheet. In particular the usual crimp seal does not allow a tight tolerance between core edge and the crimp seal, since foreign material between topsheet and backsheet would cause the crimp seal to break or not even to form.

U.S. Pat. No. 4,592,708 discloses the problem of edge definition of the core and tolerance between core edge and side seal edge. To overcome this problem this disclosure suggests to calender the absorbent core in two steps prior to combining the topsheet and the backsheet by crimping. This US patent therefore discloses an improvement step in the direction of the present invention however without satisfying the desire to approach an almost unrecognisable distance between absorbent core edge and joining edge.

Reference relating to the same subject are U.S. Pat. No. 4,888,231 and EP-A-429 393 both disclosing particular ways of calandering absorbent cores and joining the backsheet and topsheet around them. However neither of these two disclosures provides the solution provided for by the present invention.

Therefore one objective of the present invention is to provide a process by which absorbent articles, in particular sanitary napkins, can be manufactured having a crimped side seal between the topsheet and the backsheet and having sandwiched there between an absorbent core structure while the distance between the side seal and the absorbent core is minimised to a distance of not more than 6 mm with the intention to eliminate this distance.

Another objective of the present invention is to provide the process without use of additional or new equipment relative to that which is commercially available.

Yet another objective of the present invention is to provide this process for absorbent structures having a profile, that is a varying amount of absorbent material at different parts of the absorbent structure particularly having more absorbent material in the centre of the absorbent structure. Ideally this is combined with calandering to produce a uniform density of the absorbent structure despite the profile. This is achieved by so called profiled calandering using a profiled roll calender.

BRIEF DESCRIPTION OF THE INVENTION

The present invention relates to a precess to make profiled disposable absorbent products having a first sheet, a second sheet and a fibrous core. The core is disposed between the first and second sheet and both sheets are joined to each other along a continues or discontinues line. The process comprises the steps of joining the first sheet to the second sheet along a line following at least partially the periphery of the core with a distance to the core of 3 mm to 8 mm;

calandering the core between the sheets in a calender to approximately uniform density; the calandering being such that the core expands along its periphery and thereby reduces the distance of step a), preferably by 1 mm or more.

Most preferably the distance between core and the line of joining is reduced by 2 mm or more and best is a reduction to a distance of 0 mm after the calendering step.

The joining should usually be along an endless line following all around the periphery the absorbent core. The joining is preferably provided by a crimping process.

A separate calendering step prior to the joining can be included. If the absorbent core is formed on a laydown drum with pockets, then precalendering on that drum as disclosed, for example, in U.S. Pat. No. 4,592,708 or U.S. Pat. No. 4,859,388 can be included in order to further reduce the distance between core and line of joining.

DETAILED DESCRIPTION OF THE INVENTION

In the following the present invention will be described by reference to sanitary napkins as the absorbent article. However other absorbent articles like baby diapers, adult incontinence products can also be made by the process according to the present invention.

The design of sanitary napkins and the materials used in their manufacture are well known in the art. They are e.g. disclosed in EP-A-134 086, EP-A-130 848, EP-A-335 253, EP-A-336 578, WO 93/01783 and pending U.S. application Ser. No. 08/192240 of Feb. 4, 1994.

Typically sanitary napkins comprise an absorbent core made of fibrous material which optionally further comprises absorbent hydrogel particles. Such sanitary napkins cores are made by a laydown process as for example disclosed in U.S. Pat. No. 4,592,708 or U.S. Pat. No. 4,859,388. However other processes for preparing a fibrous absorbent core may also be used according to the present invention. Preferably absorbent cores are profiled to have an increased amount of absorbent material distributed towards the center relative to the periphery of the cores.

Once these absorbent cores are prepared they are placed consecutively on a conveyor belt in a spaced apart fashion. They are then sandwiched by a topsheet and a backsheet by introducing the respective roll material from above and below receptively so as to form an endless band of absorbent products. The two sheets are then joined to each other around the periphery of the absorbent core.

This joining can be provided by any of the typically processes usual in the art of making absorbent products. For sanitary napkins crimping is often used since it allows formation of the seal between topsheet and backsheet following the periphery of the absorbent core relatively close. Crimping also does not require additional materials such as adhesives.

According to the present invention a calendering step is provided after the joining of the topsheet to the backsheet which is designed to expand the absorbent core in order to approach a periphery coinciding with the line of joining between the topsheet and the backsheet.

To protect the crimp seal between the topsheet and the backsheet it is necessary to use a profiled calendering, that is a calender roll which follows the material distribution of the absorbent core so as to minimise uneven expansion of the core periphery. The profiling of the calender would typically follow the profile of the absorbent material distribution of the core. This will achieve an even expansion and prevent the splitting of the crimped seal from within. The profiled calendering can be provided by a single profile roll calender or a double calender system of a first calender of wide spacing and second roll calender of narrower spacing with profiled roll.

Optionally, but not preferably, a calendering step of the absorbent core prior to the formation of the seal between the topsheet and the backsheet can be included. This calendering can, but does not have to be, profiled.

Preferably the laydown drum calendering processes described in U.S. Pat. No. 4,592,708 and U.S. Pat. No. 4,859,388 can also be used together with the present invention.

EXAMPLE

Below a comparison between a prior art process flow and the process flow according to the invention is described. A sanitary napkin having a core of fibrous cellulose (also referred to as airfelt in the above cited disclosures) and absorbent hydrogel particles can be produced by these processes. The fibrous airfelt is carried by an air stream into which the absorbent hydrogel particles are mixed in order to create a homogeneous mixture which is formed into an absorbent core in a laydown section typically onto a laydown drum.

The absorbent cores are then calendered on the laydown drum in accordance with U.S. Pat. No. 4,592,708 or U.S. Pat. No. 4,859,388 such that the resulting absorbent cores have a width of 56 mm and a thickness of 30 mm. These cores are placed on a conveyor belt and spaced into a discontinues sequence by use of a second conveyor belt of increased speed.

The cores carried by this conveyor belt to the first calender. According to the prior art process the thickness is reduced to 10 mm which results in a product width of 54 mm due to the side expansion of the absorbent cores. According to the example of the present invention no calendering is conducted at this stage.

Together with the topsheet and the backsheet, provided below and above the absorbent cores respectively, the absorbent product is combined in the crimping section. Due to process variation the distance between the inner edges of the crimp seal on the longitudinal sides of the sanitary napkin and the core has to be 5 mm on each side for the prior art process and 2 mm on each side for the process according to the invention. 3 mm of the 5 mm are believed to be caused by the calender prior to crimping.

This results in a distance between the inner edges of the crimp seal of 58 mm+2×5 mm=68 mm for the prior art product. But only 56 mm+2×2 mm=60 mm distance is required for the product made according to the present invention due to the smaller core width prior to the crimping and the reduced variation.

The process according to the present invention then has a second calendering step which expands the absorbent core to a total width of 58 mm, leaving 1 mm on each side between the crimped seal and the absorbent core while the absorbent core thickness is reduced to 10 mm as in the prior art.

The process according to the present invention allows the use of a web width for the topsheet and the backsheet of less than the prior art process. Depending on the particular absorbent product this results in a reduced raw material consumption for all product width dependent components of up to 20% in addition to the product improvements such as absorbent core integrity and aesthetic impression.

Process Flow Example

| Prior Art | Invention |
|---|---|
| Lay down section to produce absorbent cores; e.g. cores of 56 mm width and 30 mm height | |
| First calender, profiled roll design to densify the absorbent cores; | no calender e.g. to a thickness of 10 m and a width of 58 mm |
| Crimping section to join topsheet to backsheet around the absorbent core; e.g. requiring 5 mm distance to the core edge on each side, resulting in a crimp seal distance of 58 mm + 2 × 5 mm = 68 mm | Crimping section to join topsheet to backsheet around the absorbent core; e.g. requiring 2 mm distance to the core edge on each side, resulting in a crimp seal distance of 56 mm + 2 × 2 mm = 60 mm |

What is claimed is:

1. A process for making disposable absorbent products, said products having a first sheet, a second sheet and a fibrous core, said core being disposed between said first and said second sheet and said sheets being joined to each other along a line at least partially following the periphery of said core with a reduced distance to said core; said process comprising the steps of a) joining said first sheet to said second sheet along said line following at least partially the periphery of said core with a distance from said core to said line to be about 3 mm to about 8 mm prior to calendering of said core; and b) calendering said core between said sheets in a profiled calender so that said core is expanded along its periphery and thereby said distance is reduced such that the distance of the periphery of the core to the line ranges from about 0 mm to about 3 mm.

2. The process according to claim 1 wherein said distance of the periphery of the core to the line ranges from about 0 mm to about 2 mm.

3. The process according to claim 1 wherein said core is profiled having an increased amout of absorbent material towards its center and said calender of said step b) is a profiled roll calender, which is adapted to said core profiling.

4. The process according to claim 1 wherein said sheets are joined along a line following everywhere the periphery of said core.

5. The process according to claim 1 wherein said joining of step a) is provided by crimping.

6. The process according to claim 1 wherein said core is formed on a profiled laydown drum and said process further comprises a step of pre-calendering said core on said drum.

7. The process according to any one of the preceding claims wherein said absorbent products are sanitary napkins.

8. The process according to claim 4 wherein said profiled roll calender is a double calendar system.

9. The process according to claim 1 wherein the distance of the periphery of the core to the line ranges from about 0 mm to about 1 mm.

10. The process according to claim 1 wherein the distance of the periphery of the core to the line is substantially nil.

* * * * *